United States Patent [19]

Föry et al.

[11] 4,227,914
[45] Oct. 14, 1980

[54] HERBICIDAL PHENOXYALKYLOXAZOLINES

[75] Inventors: Werner Föry, Basel; Beat Böhner, Binningen; Dieter Dürr, Bottmingen, all of Switzerland; Georg Pissiotas, Lörrach, Fed. Rep. of Germany; Otto Rohr, Therwil; Henry Szczepanski, Rheinfelden, both of Switzerland

[73] Assignee: Ciba-Geigy Corporation, Ardsley, N.Y.

[21] Appl. No.: 4,961

[22] Filed: Jan. 19, 1979

[30] Foreign Application Priority Data

Jan. 25, 1978 [CH] Switzerland .................. 804780/78

[51] Int. Cl.$^2$ .................. A01N 9/22; C07D 263/14
[52] U.S. Cl. .................. 71/88; 548/237
[58] Field of Search .................. 71/88; 260/307 F

[56] References Cited

U.S. PATENT DOCUMENTS

| | | | |
|---|---|---|---|
| 3,877,921 | 4/1975 | Timmons et al. | 71/88 X |
| 3,945,998 | 3/1976 | Anderson et al. | 71/88 X |
| 3,954,442 | 5/1976 | Becker et al. | 71/108 |
| 4,019,892 | 4/1977 | Pilgram | 71/88 |
| 4,097,581 | 6/1978 | Faroog et al. | 71/88 X |
| 4,119,633 | 10/1978 | Toth et al. | 548/237 |

Primary Examiner—Catherine L. Mills
Attorney, Agent, or Firm—Harry Falber

[57] ABSTRACT

Novel herbicidally active phenoxy-alkyloxazolines, of the formula

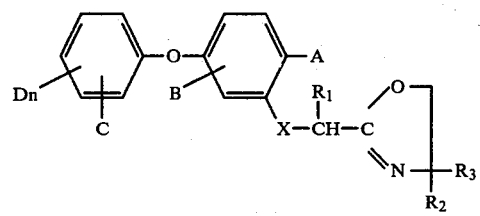

are disclosed, wherein A is hydrogen, halogen, cyano, nitro and amido or thiamido radical, B is hydrogen, $C_1$-$C_4$ alkyl, C is halogen, cyano, nitro or trifluoromethyl, amido or thiamido, D is halogen, cyano or nitro, n is 0, 1 or 2, $R_1$, $R_2$ and $R_3$, independently are hydrogen or $C_1$-$C_4$ alkyl and X is oxygen, sulfur, sulfinyl or sulfonyl.

11 Claims, No Drawings

HERBICIDAL PHENOXYALKYLOXAZOLINES

The present invention relates to novel nuclear-substituted phenoxyalkyloxazolines having herbicidal and plant growth-regulating action, processes for their production, herbicidal compositions which contain these novel compounds as active components, and to a method of selectively controlling weeds in crops of cultivated plants and of regulating plant growth which comprises the use of the novel compounds.

The compounds of the present invention have the formula

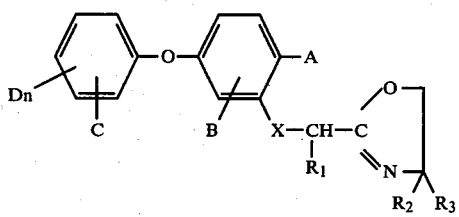
(I)

wherein
A represents hydrogen, a halogen atom, the cyano or nitro group, the amido or thiamido radical —$CONH_2$ or —$CSNH_2$,
B represents hydrogen, a halogen atom or a $C_1$–$C_4$ alkyl group,
C represents halogen, a cyano, nitro or trifluoromethyl group, the amido or thiamido radical,
D represents a halogen atom, the cyano or nitro group, n is 0, 1 or 2,
$R_1$, $R_2$ and $R_3$, each independently of the other, represents hydrogen or a $C_1$–$C_4$ alkyl group, and
X represents oxygen, sulfur, a sulfinyl or sulfonyl group —SO— or —$SO_2$—.

It is known from U.S. Pat. No. 3,877,921 and German Offenlegungsschrift No. 2,613,697 that phenoxyalkyloxazolines and phenoxyphenoxyalkyltetrazoles can be used as herbicides and growth regulators.

Surprisingly, it has now been found that the phenoxyalkyloxazolines of the formula I are very suitable for controlling dicotyledonous weeds in crops of primarily monocotyledonous plants such as cereals (wheat, barley, sorghum), rice, maize, and also individually in crops of dicotyledonous plants, such as sugar beet or soya.

It has been observed that the compounds of the present invention are particularly well tolerated by rice, both by uplant rice and transplanted lowland rice.

The compounds of the formula I are effective, inter alia, against the following dicotyledonous weeds: *Sinapis alba, Sida spinosa, Sesbania exaltata, Ipomoea purpurea, Galium aparine, Chrysanthemum leucum, Abutilon, Solanum nigrum, Ammania indica, Rotala indica* etc.

Although the novel compounds also have a good pre-emergent action, their post-emergent action is especially effective and advantageous.

A number of the active substances are also suitable for the defoliation and desiccation for example of cotton and potato plants shortly before harvesting.

The compounds of the formula I are obtained by known reaction methods of chemical synthesis.

In a first process, phenoxyalkylethyleneimides of the formula II

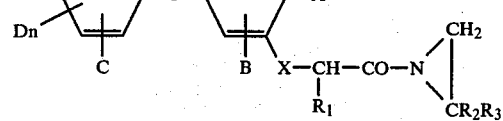
(II)

wherein $R_1$, $R_2$, $R_3$, A, B, C, D, n and X are as defined for formula I, are obtained by rearrangement of the aziridinyl amide under the influence of the iodide ion, in a solvent.

Instead of the ethyleneimide, it is also possible to subject a phenoxyalkylethylamide of the formula III

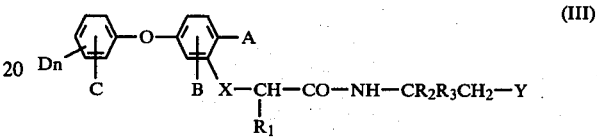
(III)

wherein $R_1$, $R_2$, $R_3$, A, B, C, D, n and X are as defined for formula I, whilst Y can be the OH group, a halogen atom or a sulfonic acid radical, to cyclisation in a solvent.

Suitable solvents are in particular aprotic water-soluble solvents, such as low molecular alcohols, ketones, dimethyl formamide, dimethyl sulfoxide, and also chlorinated hydrocarbons.

The cyclisation is carried out in the presence of a base, for example an alkali metal hydroxide or a quaternary ammonium hydroxide if Y represents a halogen atom or a sulfonic acid radical, but is carried out under acid conditions, for example in the presence of sulfuric acid, if Y represents the hydroxyl group.

Suitable catalysts for the cyclisation are the alkali metal salts or tertiary ammonium salts of halides and sulfonic acids.

The cyclisation occurs at room temperature, but the reaction mixture can be heated to the boil in order to hasten the procedure.

A further route for obtaining the phenoxyalkyloxazolines of the formula I consists in condensing a meta-phenoxyphenol of the formula IV

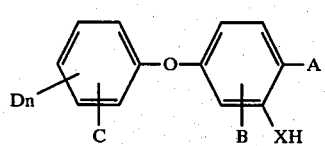
(IV)

wherein A, B, C, D and X are as defined for formula I, with a 2-oxazoline-alkyl halide of the formula V

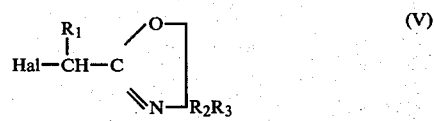
(V)

wherein Hal represents a halogen atom and $R_1$, $R_2$ and $R_3$ are as defined for formula I, in the presence of an acid acceptor.

This reaction is also carried out in a water-miscible solvent or else in a halogenated hydrocarbon, under normal pressure and at a temperature which can be between room temperature and the boiling point of the reaction mixture. Preferably, the reaction mixture is refluxed.

The acid acceptor can be an aqueous alkali metal hydroxide, such as KOH and NaOH, and also another base, such as ammonia, a carbonate ($K_2CO_3$, $NaHCO_3$), an alcoholate ($NaOCH_3$, potassium tert-butylate), and also an organic base, such as triethylamine etc. If an organic base is already employed as solvent, for example pyridine, then it acts simultaneously as acid acceptor.

The starting materials of the formula II are most desirably obtained by amidation from the corresponding phenoxyphenoxypropionic acids described for example in Swiss patent application No. 2867/77.

The amidation is carried out by methods which are in themselves known by reacting the halides or the anhydride of these acids with ethyleneimine, the corresponding haloethylamines, or with a 2-amino-ethyl sulfonate.

The starting materials of the formula V are known or they can be easily prepared by conventional methods. Many starting phenols of the formula IV are also already known.

Phenoxyphenols of the formula IV which have not yet been described can be easily prepared by conventional methods and techniques, for example as described in German Offenlegungsschriften Nos. 2,433,066 and 2,433,067.

Starting phenols of the formula IV, wherein A represents the cyano group or a halogen atom, are advantageously obtained from the corresponding nitro compounds (Am. Soc. 52, 1208 (1930) or from the aromatic amines obtained therefrom via the diazonium salts.

Accordingly, for example, a 2-methoxy-4-chloronitrobenzene of the formula

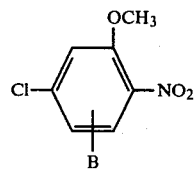
(VI)

wherein B is as defined for formula I, can be reacted with a phenol of the formula VII

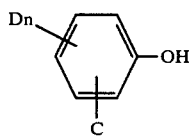
(VII)

wherein C, D and n are as defined for formula I, in an alkaline medium, to give the compound of the formula VIII

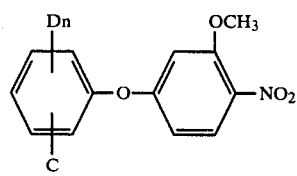
(VIII)

for example in accordance with the particulars of German Offenlegungsschrift No. 2,304,006.

The same nitro compound is also obtained by reaction of 2 moles of a phenol of the formula VII with 2,4-dichloronitrobenzene. In this reaction, a compound of the formula

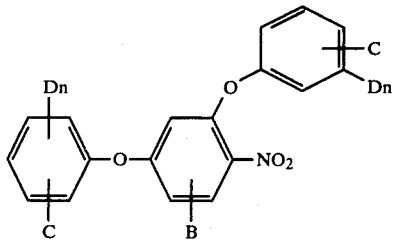

wherein B, C, D and n are as defined for formula I, is formed as intermediate, which is then "transetherified" by heating with methanol and KOH in dioxane to give the methoxy compound VIII (method described in German Offenlegungsschrift No. 2,533,172).

The resulting nitrated intermediate is reacted by a conventional reduction of the nitro group to give the corresponding amine, which is then converted into the diazonium salt (e.g. diazonium chloride). Finally, the diazo group of the diazonium salt is replaced by conventional methods by the cyano group or a halogen atom or by another substituent in accordance with the definition of A.

The reduction of the nitro group in compounds of the formula VII is carried out catalytically with hydrogen (for example with Raney nickel) in solution in an inert solvent, or by gradual addition of a 2-oxazoline alkyl halide of the formula V to a mixture of iron powder and dilute hydrochloric acid at elevated temperature.

The diazotisation of the resulting amine is effected in conventional manner in solution in dilute hydrochloric acid by the dropwise addition of an aqueous $NaNO_2$ solution at a temperature below 5° C.

The substitution of the cyano group for the diazo group is carried out by the dropwise addition of the disodium salt to an aqueous solution of $K_3[Cu(CN)_4]$ or by addition of copper powder and copper(I) cyanide to the solution of the diazonium salt. These reactions to give p-cyano-diphenyl ethers, starting from substituted p-nitro-diphenyl ethers, have already been described in German Offenlegungsschrift No. 1,912,600. The cyano group can subsequently be converted into the amido or thioamido group.

The substitution of chlorine for the diazo group is effected by addition of copper(I) chloride (CuCl) or finely divided copper powder to the diazonium chloride solution.

The substitution of bromine for the diazo group is most expediently effected by the addition of KBr and CuBr to a diazonium salt solution, whilst the substitution of iodine for the diazo group can be carried out by treating the diazonium salt with potassium iodide.

In order finally to obtain the corresponding free starting phenol of the formula IV the ether protective group in the meta-position (—O—$CH_3$) is cleaved, for example with HBr in glacial acetic acid.

The production of a number of phenoxyalkyloxazolines of the formula I is illustrated in the following Examples. Further active compounds obtained in corresponding manner are listed in the subsequent table.

EXAMPLE 1

2-[1-[3'-(2'',4''-Dichlorophenoxy)-6'-chlorophenoxy]-ethyl]-oxazoline

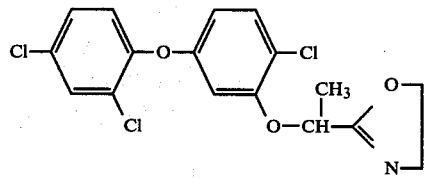

A suspension of 20.3 g of 2,4,4'-trichloro-3'-hydroxydiphenyl ether, 16.5 g of α-bromopropionic acid 2-chloroethylamide and 21.2 g of anhydrous potassium carbonate in 200 ml of methyl ethyl ketone is stirred for 18 hours at reflux temperature. The reaction mixture is filtered and the filtrate is concentrated in vacuo. The oily residue (30.1 g) is dissolved in 105 ml of methylene chloride and, after the addition of 3.57 g of tetrabutylammonium hydrogen sulfate and 35 ml of 10% aqueous sodium hydroxide, the solution is stirred for 2 hours at room temperature. The methylene chloride phase is separated, washed with water, dried, and concentrated in vacuo, affording 26.4 g of the title compound in the form of an oil, which is triturated with a small amount of alcohol and solidifies to a crystalline substance. Melting point: 85°–86° C.

EXAMPLE 2

2-[1-[3'-(2',4''-Dichlorophenoxy)-6'-chlorophenoxy]-ethyl]-4,4-dimethyl oxazoline

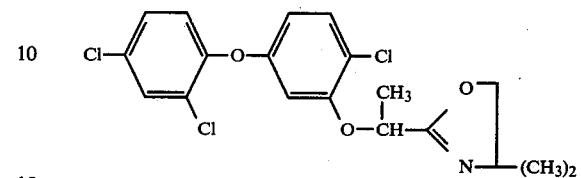

With stirring, 50 g of α-[3-(2',4'-dichlorophenoxy)-6-chlorophenoxy]-propionic acid 1,1-dimethyl-2-hydroxyethylamide are added to 50 ml of thionyl chloride. After the exothermic reaction has subsided, the reaction mixture is allowed to stand for 2 hours at room temperature and, after addition of 100 ml of toluene, concentrated in vacuo. The residue is dissolved in 250 ml of methylene chloride, then 60 g of pulverised sodium hydroxide and 4 g of benzyltriethylammonium chloride are added and the mixture is stirred for 30 minutes under nitrogen at room temperature. The solution is filtered through Celite and concentrated. The residue is dissolved in 500 ml of ether, washed with two 200 ml portions of saturated $Na_2CO_3$ solution, dried and concentrated, affording 43.5 g of the oxazoline. Melting point: 111°–112° C.

| Compound | A | B (pos.) | C (pos.) | D (pos.) | $R_1$ | $R_2$ | $R_3$ | Physical constant (°C.) |
|---|---|---|---|---|---|---|---|---|
| 3 | $NO_2$ | | Cl(2') | Cl(4') | $CH_3$ | | | m.p. 110°–120° |
| 4 | CN | | Cl(2') | Cl(4') | $CH_3$ | | | |
| 5 | Br | | Cl(2') | Cl(4') | $CH_3$ | | | m.p. 70°–80° |
| 6 | Cl | | Cl(2') | $CF_3$(4') | $CH_3$ | | | m.p. 96°–98° |
| 7 | Cl | | Cl(2') | $CF_3$(4') | $CH_3$ | $CH_3$ | $CH_3$ | m.p. 55° |
| 8 | $NO_2$ | | Cl(2') | $CF_3$(4') | $CH_3$ | | | $n_D^{35}$ 1.5450 |
| 9 | Cl | | Cl(2') | Br(4') | $CH_3$ | | | |
| 10 | Br | | Cl(2') | Br(4') | $CH_3$ | | | |
| 11 | CN | | Cl(2') | $CF_3$(4') | $CH_3$ | | | $n_D^{24}$ 1.5340 |
| 12 | Cl | Cl(4) | Cl(2') | $CF_3$(4') | $CH_3$ | | | oil |
| 13 | | Cl(4) | Cl(2') | $CF_3$(4') | | | | |
| 14 | Cl | Cl(4) | CN(2') | $CF_3$(4') | $CH_3$ | | | oil |
| 15 | $NO_2$ | Cl(4) | Cl(2') | $CF_3$(4') | $CH_3$ | | | m.p. 50°–59° |
| 16 | $NO_2$ | Cl(4) | Cl(2') | Cl(4') | $CH_3$ | | | oil |
| 17 | | $CH_3$(5) | Cl(2') | $CF_3$(4') | $CH_3$ | | | |
| 18 | Br | | Cl(2') | $CF_3$(4') | $CH_3$ | | | oil |
| 19 | Cl | | CN(2') | Cl(4') | $CH_3$ | | | |
| 20 | CN | | CN(2') | Cl(4') | $CH_3$ | | | |
| 21 | $NO_2$ | | CN(2') | Cl(4') | $CH_3$ | | | |
| 22 | Cl | | CN(2') | $CF_3$(4') | $CH_3$ | | | m.p. 130°–136° |
| 23 | CN | | CN(2') | $CF_3$(4') | $CH_3$ | | | |
| 24 | $NO_2$ | | CN(2') | $CF_3$(4') | $CH_3$ | | | |
| 25 | Cl | | | $CF_3$(4') | $CH_3$ | | | oil |
| 26 | CN | | | $CF_3$(4') | $CH_3$ | | | |
| 27 | $NO_2$ | | | $CF_3$(4') | $CH_3$ | | | oil |
| 28 | Cl | | Cl(2') | Cl(4') | H | | | |
| 29 | Cl | | Cl(2') | $CF_3$(4') | H | | | |
| 30 | $NO_2$ | | Cl(2') | $CF_3$(4') | H | | | |
| 31 | $NO_2$ | | Cl(2') | $Cl_3$(4') | H | | | |
| 32 | Cl | | Cl(2') | Cl(4') | H | $CH_3$ | $CH_3$ | |
| 33 | $NO_2$ | | CN(2') | | $CH_3$ | $CH_3$ | | m.p. 98°–101° |

-continued $$\text{structure: D-(C ring)-O-(B ring, substituent A)-S-CH(R}_1\text{)-C(=N-R}_2\text{)(O-R}_3\text{)}$$

| | D | C | B | A | |
|---|---|---|---|---|---|
| 32 | Cl | Cl(2') | Cl(4') | CH$_3$ | oil |
| 33 | Cl | Cl(2') | CF$_3$(4') | CH$_3$ | oil |
| 34 | | Cl(2') | CF$_3$(4') | CH$_3$ | |
| 35 | | Cl(2') | Cl(4') | CH$_3$ | |

The novel active substances of the formula I are stable compounds which are soluble in conventional organic solvents, such as alcohols, ethers, ketones, dimethyl formamide, dimethyl sulphoxide etc.

The compositions of the present invention are obtained in known manner by intimately mixing and grinding active substances of the general formula I with suitable carriers and/or additives, with or without the addition of antifoam agents, wetting agents, dispersants and/or solvents which are inert to the active substances. The active substances can be processed to the following formulations:

solid formulations: dusts, tracking powders, granules (coated granules, impregnated granules and homogeneous granules);
active substance concentrates which are dispersible in water: wettable powders, pastes, emulsions, emulsion concentrates;
liquid formulations: solutions.

The concentrations of active substance in the compositions of this invention are between 1 and 80 percent by weight. As circumstances may require, the active substances can also be applied in low concentrations of about 0.05 to 1 percent by weight.

The compositions of the present invention can be mixed with other biocidal active substances or compositions. The following formulation Examples will serve to illustrate the production of compositions of the invention (parts are by weight).

GRANULES

The following substances are used to formulate 5% granules:
5 parts of one of the active substances of the formula I,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone, and the polyethylene glycol and cetyl polyglycol ether are then added. The resultant solution is sprayed on kaolin and subsequently evaporated in vacuo.

WETTABLE POWDER

The following constituents are used to formulate (a) a 70% and (b) a 10% wettable powder:

(a)

70 parts of an active substance of the formula I,
5 parts of sodium dibutylnaphthalenesulfate,
3 parts of naphthalenesulfonic acid/phenolsulfonic acid/formaldehyde condensate (3:2:1),
10 parts of kaolin,
12 parts of Champagne chalk;

(b)

10 parts of an active substance of the formula I,
3 parts of a mixture of the sodium salts of saturated fatty alcohol sulfates,
5 parts of naphthalenesulfonic acid/formaldehyde condensate,
82 parts of kaolin.

The respective active substance is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active substance. These suspensions are suitable for controlling weeds in cultivations of plants.

PASTE

The following substances are used to formulate a 45% paste:
45 parts of an active substance of the formula I,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to manufacture suspensions of the desired concentration of active substance.

EMULSIFIABLE CONCENTRATE

The following ingredients are mixed to formulate a 25% emulsion concentrate:
25 parts of an active substance of the formula I,
5 parts of a mixture of nonylphenolpolyoxyethylene and calcium dodecylbenzenesulfonate,
35 parts of 3,3,5-trimethyl-2-cyclohexen-1-one,
35 parts of dimethylformamide.

This concentrate can be diluted with water to give emulsions in suitable concentrations of e.g. 0.1 to 10%. Such emulsions are suitable for controlling weeds in crops of plants.

The novel phenoxyalkyloxazolines of the formula I and the compositions which contain them have an excellent selective herbicidal action against weeds in different crops of cultivated, preferably monocotyledonous plants, and in addition they exert a plant growth-regulating action.

A particularly preferred field of use is the selective control of dicotyledonous weeds, for example in cereal crops, especially in rice and also in soya.

Although the novel active substances of the formula I are effective in pre- and post-emergent application, the post-emergent application as contact herbicide is preferred, although the pre-emergent use is also of interest.

The novel active compounds of the formula I are preferably formulated for example to 25% wettable powders or for example to 20% emulsifiable concentrates, and, diluted with water, applied to the crops of plants in the post-emergent stage.

HERBICIDAL ACTION ON POST-EMERGENT APPLICATION OF THE ACTIVE COMPOUNDS

Different cultivated plants and weeds are reared from seeds in pots in a greenhouse until they have reached the 4- to 6-leaf stage. Then the plants are sprayed with an aqueous active substance emulsion (obtained from a 25% emulsifiable concentrate) corresponding to a rate of application of 4 kg per hectare. The treated plants are then kept at optimum light, watering, temperature (22°–25° C.) and humidity (50–70% relative humidity) conditions. Evaluation of the test was made 15 days after treatment. The state of the plants is examined and rated as follows:
1 plant not germinated or totally withered
2–3 strong action
4–6 average action
7–8 slight action
9 no action, i.e. as untreated control
plant not tested with corresponding active substance.

The results are reported in the following table

| Plant | Tested compound | | | | | | |
|---|---|---|---|---|---|---|---|
| | 1 | 2 | 6 | 7 | 8 | 22 | 33 | A |
| Phaseolus vulgaris | 1 | 3 | 1 | — | 1 | 3 | — | 9 |
| Sinapis alba | 1 | 3 | 1 | 1 | 1 | 1 | 2 | 7 |
| Solanum lycopersicum | 1 | 1 | 1 | 1 | 1 | 1 | 1 | 4 |

Compound A=5-[1'-[para-trifluoromethylphenoxyphenoxy)-ethyl]-tetrazole of the formula

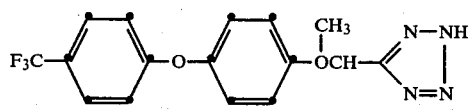

known from German Offenlegungsschrift No. 2,613,697.

In a further test, the plants are sprayed in the 4- to 6-leaf stage with dilute active substance dispersions in rates of application of 0.5, 1 and 2 kg per hectare respectively. The plants are then kept also for 15 days in a greenhouse at 24°–26° C. and 45–60% relative humidity before the test is evaluated in accordance with the above rating. The results are reported in the following table

| tested compound rate of application in kg/ha | No. 1 | | | 6 | | | 22 | | | B | | |
|---|---|---|---|---|---|---|---|---|---|---|---|---|
| | 0.5 | 1 | 2 | 0.5 | 1 | 2 | 0.5 | 1 | 2 | 0.5 | 1 | 2 |
| Plant | | | | | | | | | | | | |
| Abutilon sp | 2 | 1 | 1 | 1 | 1 | 1 | — | — | 1 | 7 | 6 | 6 |
| Amaranthus retroflexus | 1 | 1 | 1 | 1 | 1 | 1 | — | — | 1 | 3 | 2 | 2 |
| Galium aparine | 3 | 2 | 2 | 2 | 1 | 1 | — | — | 4 | 9 | 8 | 4 |
| Sinapis alba | 2 | 1 | 1 | 1 | 1 | 1 | — | — | 1 | 2 | 2 | 2 |

B=2-[1'-(4''-chloro-2''-methylphenoxy)-ethyl]-oxazoline of the formula

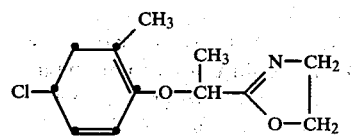

known from U.S. Pat. No. 3,877,921.

SELECTIVE HERBICIDAL ACTION ON RICE IN POST-EMERGENT APPLICATION

Twenty-five-day-old rice plants are transplanted into large rectangular asbestos cement containers in a greenhouse. Seeds of the weeds occurring in rice crops, namely Echinochloa crus galli, Cyperus difformis, Ammania indica, and Rotala indica, are then sown between the rows of rice plants. The containers are well watered and kept at a temperature of about 25° C. and at high humidity. Twelve days later, when the weeds have emerged and reached the 2–3 leaf stage, the soil in each of the containers is covered with a layer of water to a height of 2.5 cm. The active substance is then applied in the form of an emulsifiable concentrate with a pipette between the rows of plants. The emulsifiable concentrate is diluted and applied so that it corresponds to a field application rate of 4, 2, 1 and 0.5 kg respectively of active substance per hectare. The test is evaluated 4 weeks later. In this test, compound 1 caused severe damage to the dicotyledonous weeds Ammania indica and Rotala and appreciable damage to the grass Cyperus. Echinochloa crus galli was only slightly damaged. The rice suffered no damage.

What is claimed is:
1. Phenoxyalkyloxazolines of the formula I

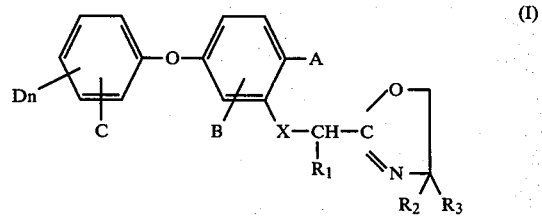

wherein
A represents hydrogen, a halogen atom, the cyano or nitro group, the amido or thiamido radical —CONH$_2$ or —CSNH$_2$,
B represents hydrogen, a halogen atom or a C$_1$–C$_4$ alkyl group, C represents halogen, a cyano, nitro or trifluoromethyl group, the amido or thiamido radical, D represents a halogen atom, the cyano or nitro group, n is 0, 1 or 2, $R_1$, $R_2$ and $R_3$, each independently of the other, represents hydrogen or a $C_1$-$C_4$ alkyl group, and X represents oxygen or sulfur.

2. Phenoxyalkyloxazolines according to claim 1, wherein C does not represent hydrogen and is the in the ortho-position to the oxygen atom and D is in the para-position to the oxygen atom, and n is 1.

3. Phenoxyalkyloxazolines according to claim 1, wherein $R_1$ represents methyl and $R_2$ and $R_3$ represent hydrogen.

4. 2-[1-[3'-(2'',4''-Dichlorophenoxy)-6-chlorophenoxy]-ethyl]-oxazoline.

5. 2-[1[3'-(2''-chloro-4''-Trifluoromethylphenoxy)-6'-chlorophenoxy]-ethyl]-oxazoline.

6. 2-[1-[3'-(2''-Chloro-4''-trifluoromethylphenoxy)-6'-nitrophenoxy]-ethyl]-oxazoline.

7. A herbicidal composition which contains as active component a herbicidally effective amount of a phenoxyalkyloxazoline of the formula I of claim 1, together with a suitable carrier therefor.

8. A method of selectively controlling weeds in crops of cultivated plants, which comprises applying to the areas under cultivation a herbicidally effective amount of a phenoxyalkyloxazoline of the formula I of claim 1.

9. The method according to claim 8, which comprises applying to the areas under cultivation in post-emergent application a herbicidally effective amount of 2-[1-[3'-(2',4''-dichlorophenoxy)-6'-chlorophenoxy]-ethyl]-oxazoline.

10. The method according to claim 8, which comprises applying to the areas under cultivation in post-emergent application a herbicidally effective amount of 2-[1-[3'-(2'chloro-4''-trifluoromethylphenoxy)-6'-chlorophenoxy]-ethyl]-oxazoline.

11. A method according to claim 8 for the post-emergent control of dicotyledonous weeds in soya crops.

* * * * *